United States Patent [19]

Hagen et al.

[11] Patent Number: 4,497,651
[45] Date of Patent: Feb. 5, 1985

[54] DICHLOROQUINOLINE DERIVATIVES FOR USE AS HERBICIDES

[75] Inventors: Helmut Hagen, Frankenthal; Juergen Markert, Mutterstadt; Bruno Wuerzer, Otterstadt, all of Fed. Rep. of Germany

[73] Assignee: BASF Aktiengesellschaft, Fed. Rep. of Germany

[21] Appl. No.: 349,675

[22] Filed: Feb. 17, 1982

[51] Int. Cl.³ ............... A01N 43/42; C07D 215/12; C07D 215/14; C07D 215/48

[52] U.S. Cl. ........................... 71/94; 71/92; 544/128; 544/363; 546/168; 546/169; 546/170; 546/176; 546/180; 546/174; 546/175

[58] Field of Search ............. 546/168, 169, 170, 174, 546/175, 180, 176; 71/94, 92; 544/128, 363

[56] References Cited

U.S. PATENT DOCUMENTS 2,507,146  5/1950  Dickey et al. ............ 546/169 X
2,661,276 12/1953  Schlesinger et al. ............ 71/2.5
2,665,203  1/1954  Emerson et al. ............ 546/180 X
3,335,151  8/1967  Holtschmidt et al. ............ 71/94 X
4,036,963  7/1977  Gialdi et al. ............ 546/169 X

FOREIGN PATENT DOCUMENTS 1424359  2/1976  United Kingdom .

OTHER PUBLICATIONS

Hamada et al., Chemical Abstracts, vol. 88, 190564z, (1978).

Primary Examiner—Paul M. Coughlan, Jr.
Attorney, Agent, or Firm—Keil & Weinkauf

[57] ABSTRACT

Dichloroquinoline derivatives of the formula

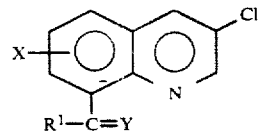

are prepared as described, and are used as herbicides.

11 Claims, No Drawings

DICHLOROQUINOLINE DERIVATIVES FOR USE AS HERBICIDES

The present invention relates to dichloroquinoline derivatives, a process for their preparation, herbicides containing these compounds and methods of controlling undesirable plant growth using these compounds.

Quinoline compounds, eg. 7-chloroquinoline (German Laid-Open Application DOS No. 2,322,143) and 4-chloro-3-nitroquinoline (U.S. Pat. No. 2,661,276), have been disclosed as herbicides which have selective, properties and can also be used for total vegetation control. The different levels of action are remarkable; introduction of the carboxyl group, for example as in 7-chloro-4-hydroxyquinoline-2-carboxylic acid, leads to a substantial loss in activity in comparison with 7-chloro-4-hydroxyquinoline and other derivatives of this type (U.S. Pat. No. 2,661,276).

We have found that dischloroquinoline derivatives of the formula I

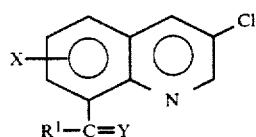

where X is chlorine in the 5-, 6- or 7-position, Y is oxygen, sulfur, hydroxyimino, two hydrogen atoms, two chlorine atoms or =N—A—B, where A is a direct bond or $CH_2$ and B is a phenyl or pyridine radical which is unsubstituted or substituted by chlorine, nitro, methyl, trifluoromethyl or methoxy, and $R^1$ is hydrogen, halogen, cyano or $-NR^2R^3$, where $R^2$ and $R^3$ are identical or different and each is hydrogen, $C_1$-$C_6$-alkyl, $C_1$-$C_6$-alkenyl, $C_1$-$C_6$-hydroxyalkyl, formyl, cyclohexyl, phenyl or pyridinyl, or $R^2$ and $R^3$ together are $(CH_2)_4$ or $(CH_2)_5$, it being possible for one $CH_2$ group to be replaced by oxygen, nitrogen or N—$CH_3$, or $R^1$ is COOH or OM, where M is a metal of main group 1 or 2 of the Periodic Table, hydrogen, $C_1$-$C_8$-alkyl, phenyl which is unsubstituted or substituted by halogen, nitro, $C_1$-$C_4$-alkyl or trihalomethyl, or $H_2N^{\oplus}R^2R^3$, where $R^2$ and $R^3$ have the above meanings, or Y and $R^1$, together with the carbon atom, are nitrile, have a good herbicidal action.

Preferably, in formula I, X is chlorine in the 7-position, $R^1$ is hydrogen, OH, ONa, $ON^{\oplus}H_2(CH_3)_2$ or NHCHO and Y is oxygen, two chlorine or hydrogen atoms or

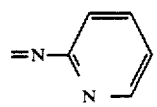

The novel compounds are obtained when a compound of the formula II

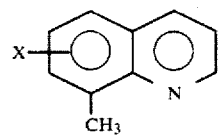

where X has the above meanings, is chlorinated at from 140° to 190° C. using a free radical initiator and with exclusion of light, and, if desired, the resulting compound of the formula III

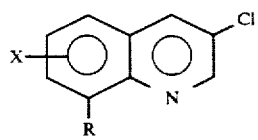

where X has the same meanings as above and R is chloromethyl, dichloromethyl or trichloromethyl, is converted into a compound of the formula I where $R^1$—C=Y is other than R.

The 8-methylquinolines used in the process according to the invention are known compounds. Their preparation has been described, for example, by Bradford in J. Chem. Soc. 1947, 437, and by Irving in J. Amer. Chem. Soc. 72, (1950), 4059.

Prior art chlorination of N-containing heterocyclic compounds is effected in acetic acid or sulfuric acid (cf. Houben-Weyl, Volume V/3, pages 725 f, Georg Thieme Verlag, 1962), and, in the case of side-chain chlorination, under UV light (cf. Houben-Weyl, Volume V/3, page 747, Georg Thieme Verlag, 1962).

Surprisingly, in the case of 8-methylquinolines, it is possible simultaneously to effect specific nuclear chlorination in the 3-position as well as side-chain chlorination by suitable choice of the reaction parameters. With the chosen reaction parameters and by adjusting the amount of chlorine and the chlorination time, the reaction can be conducted exactly, permitting selective preparation of the chloromethyl, dichloromethyl or trichloromethyl compound.

The chlorination is carried out in an inert solvent, eg. a dichlorobenzene or trichlorobenzene, in the presence of a free radical initiator, eg. azoisobutyronitrile or benzoyl peroxide, with exclusion of light, at from 140° to 190° C., preferably from 150° to 160° C. Nuclear chlorination no longer takes place above 190° C.

The compounds where Y is oxygen are obtained by treating the corresponding dichloro compound with a strong acid, such as concentrated sulfuric acid or concentrated hydrochloric acid, at from 50° to 150° C.

The compounds where Y is sulfur are obtained by reacting the corresponding nitrile with hydrogen sulfide in a basic solvent, preferably pyridine.

The compounds where Y is hydroxyimino are obtained by heating the corresponding aldehyde with hydroxylamine at from 50° to 150° C. If hydroxylamine hydrochloride or hydroxylammomium sulfate is used instead of free hydroxylamine, a base must be added. Suitable bases are sodium carbonate, sodium bicarbonate, sodium hydroxide solution and the corresponding potassium compounds.

The compounds where Y is =N—A—B are obtained from the corresponding aldehyde and the compound $H_2N$—A—B by heating at from 50° to 150° C. in a solvent, such as an alcohol or open-chain or cyclic aliphatic ether.

The compounds where $R^1$ is cyano are obtained by reacting the corresponding chloro compound with potassium cyanide or sodium cyanide in a solvent, such as dimethylformamide or dimethylsulfoxide, at from 100° to 200° C. in the presence of a little potassium iodide.

The compounds where $R^1$ is $NR^2R^3$ are obtained by reacting the corresponding amide with the corresponding chloro compound at from 30° to 100° C. in the presence or absence of a solvent, such as an alcohol, an ether, or dimethylsulfoxide.

The ammonium compounds are obtained by reacting the corresponding carboxylic acid with an amine, for example in an alcohol or dimethylformamide or dimethylsulfoxide, at from 50° to 150° C.

The compounds where $R^1$ is COOH are obtained, for example, by hydrolyzing the corresponding nitrile with concentrated sulfuric acid.

The compounds where $R^1$ is OH are obtained by reacting the corresponding chloro compound with sodium hydroxide or potassium hydroxide.

The Examples which follow illustrate the preparation of the novel compounds:

EXAMPLE 1

89 parts of 7-chloro-8-methylquinoline and 0.5 part of azobisisobutyronitrile were introduced into 500 parts of dichlorobenzene and the mixture was heated to 140° C. Introduction of 80 parts of chlorine was started at this temperature the temperature being increased to 160° C. during this operation. After the addition of chlorine, the solution was flushed with nitrogen, most of the solvent was distilled off and the precipitated solid was filtered off with suction and washed with petroleum ether. 113 parts of 3,7-dichloro-8-chloromethylquinoline of melting point 129° C. were obtained. The yield corresponds to 93% of theory.

EXAMPLE 2

177 parts of 7-chloro-8-methylquinoline and 1 part of azobisisobutyronitrile were introduced into 1,000 parts of dichlorobenzene and the mixture was heated to 140° C. Introduction of 250 parts of chlorine started at this temperature. The temperature was increased to 175° C. When the reaction has ended, the solution was flushed with nitrogen and then most of the solvent was distilled off and the precipitated solid was filtered off with suction and washed with petroleum ether. 255 parts of 3,7-dichloro-8-dichloromethylquinoline of melting point 154° C. were obtained. The yield corresponds to 80% of theory.

EXAMPLE 3

35 parts of 6-chloro-8-methylquinoline and 0.5 part of azobisisobutyronitrile in 200 parts of dichlorobenzene were heated to 140° C. Introduction of 70–90 parts of chlorine was started at this temperature, whilst the temperature was increased to 180° C. When the reaction had ended, the solution was flushed with nitrogen, the solvent was distilled off and the residue was recrystallized from naphtha. 52 parts of 3,6-dichloro-8-trichloromethylquinoline of melting point 198° C. were obtained. The yield corresponds to 82% of theory.

EXAMPLE 4

56 parts of 3,7-dichloro-8-dichloromethylquinoline in 250 parts of 90% strength sulfuric acid were stirred at 100° C. for 6 hours. After cooling, the solution was poured onto ice and the precipitated solid was filtered off with suction, washed neutral with water and dried. 195 parts of 3,7-dichloroquinoline-8-carbaldehyde of melting point 208° C. were obtained. The yield corresponds to 87% of theory.

EXAMPLE 5

22.6 parts of 3,7-dichloroquinoline-8-carbaldehyde (Example 4) were dissolved in 300 parts of alcohol. 10.6 parts of sodium carbonate and 6.9 parts of hydroxylammonium chloride were added to this solution and the suspension was refluxed for 1 hour. 1,000 parts of water were then added and the precipitated solid was filtered off and dried. 23 parts of 3,7-dichloro-8-hydroxyiminoquinoline of melting point 202° C. were obtained. The yield corresponds to 96% of theory.

EXAMPLE 6

24.6 parts of 3,7-dichloro-8-chloromethylquinoline and 30 parts of diethylamine were stirred at 55° C. for 6 hours. Water was added and the solid was filtered off with suction and dried. 25 parts of 3,7-dichloro-8-diethylaminomethylquinoline of melting point 54° C. were obtained. The yield corresponds to 89% of theory.

EXAMPLE 7

24.6 parts of 3,7-dichloro-8-chloromethylquinoline (Example 1) and 15 parts of sodium p-chlorophenate in 200 parts of dimethylformamide were stirred at 100° C. for 10 hours. The solvent was distilled off, water was added to the residue and the solid was filtered off with suction, dried and recrystallized from a suitable solvent. 32 parts of 3,7-dichloro-8-p-chlorophenoxymethylquinoline of melting point 110° C. were obtained. The yield corresponds to 95% of theory.

EXAMPLE 8

49 parts of 3,7-dichloro-8-chloromethylquinoline (Example 1), 13 parts of potassium cyanide and 0.1 part of potassium iodide in 300 parts of dimethylformamide were heated at 150° C. for 4 hours. Water was added to the reaction solution and the precipitated product was filtered off with suction and recrystallized from methylglycol. 32 parts of 3,7-dichloro-8-cyanomethylquinoline of melting point 152° C. were obtained. The yield corresponds to 67% of theory.

EXAMPLE 9

28.1 parts of 3,7-dichloro-8-chloromethylquinoline (Example 1), 6.95 parts of hydroxylamine hydrochloride and 13.6 parts of sodium formate in 200 ml of formic acid and 60 ml of water were stirred at 100° C. for 12 hours. The reaction solution was poured onto ice and the precipitated solid was filtered off with suction, washed neutral with water and dried. 19 parts of 3,7-dichloro-8-cyanoquinoline of melting point 222° C. were obtained. The yield corresponds to 78.5% of theory.

EXAMPLE 10

200 parts of 3,7-dichloro-8-cyanoquinoline (Example 9) in 2,600 parts of 65% strength sulfuric acid were stirred at 140° C. for 20 hours. The cooled solution was poured onto ice, the precipitated solid was filtered off with suction, dried, and taken up in dimethylformamide, active charcoal was added, the mixture was filtered, water was added to the filtrate and the solid was filtered off with suction, washed with water and dried. 200 parts of 3,7-dichloroquinoline-8-carboxylic acid of melting point 272° C. were obtained. The yield corresponds to 92% of theory.

EXAMPLE 11

20 parts of 3,5-dichloroquinoline-8-carbaldehyde (prepared by a method similar to that in Example 4) and 14.6 parts of 2,4-dichloroaniline in 300 parts of alcohol were refluxed for 3 hours. The solution was cooled and the precipitated product was filtered off with suction and recrystallized from methylglycol. 30 g of 3,5-dichloro-8-(2,4-dichlorophenyliminomethyl)-quinoline of melting point 156° C. were obtained. The yield corresponds to 90% of theory.

EXAMPLE 12

24.6 parts of 3,7-dichloro-8-chloromethylquinoline (Example 1) in 300 parts of formamide were refluxed for 5 hours. Water was added and the solid was filtered off with suction and recrystallized from methanol. 23 parts of 3,7-dichloro-8-formylaminomethylquinoline of melting point 110° C. were obtained. The yield corresponds to 94% of theory.

EXAMPLE 13

22 parts of 3,6-dichloro-8-cyanoquinoline (prepared by a method similar to that in Example 8) in 80 parts of triethylamine and 80 parts of pyridine were heated at 40° C., and $H_2S$ gas was slowly passed in for 4 hours. Water was then added and the solid was filtered off with suction, washed with water and acetone and recrystallized from ethyl acetate. 17 parts of 3,6-dichloroquinoline-8-thiocarboxylic acid amide of melting point 226° C. were obtained. The yield corresponds to 66% of theory.

The following compounds were prepared or can be prepared analogously to Examples 1 to 12:

| Ex. | X | Y | $R^1$ | M.p. [°C.] |
|---|---|---|---|---|
| 14 | 7-Cl | =N—(2-pyridyl) | H | 104 |
| 15 | 7-Cl | O | 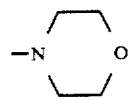 | 206 |
| 16 | 7-Cl | O | $OC_3H_7$ | 112 |
| 17 | 7-Cl | H,H | $O-(4-CH_3-C_6H_4)$ | 88–90 |
| 18 | 7-Cl | H,H | $O-(2,4-DiNO_2-C_6H_3)$ | 144 |
| 19 | 7-Cl | H,H | $O-(2,4-DiCl-C_6H_3)$ | 134 |
| 20 | 7-Cl | H,H | $O-(4-CH_3O-C_6H_4)$ | 155 |
| 21 | 7-Cl | H,H | $O-(2-NO_2-C_6H_4)$ | 167–168 |
| 22 | 7-Cl | H,H | $O-(3-NO_2-C_6H_4)$ | 140–142 |
| 23 | 7-Cl | H,H | $O-(C_6H_5)$ | — |
| 24 | 7-Cl | H,H | $O-(4-Br-C_6H_4)$ | — |
| 25 | 7-Cl | H,H | $O-(4-CCl_3-C_6H_4)$ | — |
| 26 | 7-Cl | H,H | $OC_4H_9$ | — |
| 27 | 7-Cl | H,H | $OC_5H_{11}$ | — |
| 28 | 7-Cl | H,H | $O_6H_{13}$ | — |
| 29 | 7-Cl | H,H | $OCH_3$ | 78 |
| 30 | 7-Cl | H,H | $OC_2H_5$ | — |
| 31 | 7-Cl | H,H | $O-iso-C_3H_7$ | — |
| 32 | 7-Cl | O | $N(C_2H_5)_2$ | 145 (.3$H_2O$) |
| 33 | 7-Cl | O | 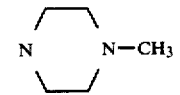 | 223 |
| 34 | 7-Cl | O | $NH_2$ | 238 |
| 35 | 7-Cl | O | $N(CH_2-CH_2OH)_2$ | — |
| 36 | 7-Cl | O | $N(CH_2-CH=CH_2)_2$ | — |
| 37 | 7-Cl | O | 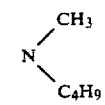 | — |
| 38 | 7-Cl | O | $N(CH-C=CH_2)_2$ <br> $\|$ <br> $CH_3$ | — |
| 39 | 7-Cl | O | N—piperidinyl | — |
| 40 | 7-Cl | O | N—pyrrolidinyl | — |
| 41 | 7-Cl | O | $NHCH_3$ | — |
| 42 | 7-Cl | O | $NH-C_6H_5$ | — |
| 43 | 7-Cl | S | $NH_2$ | — |
| 44 | 7-Cl | S | $N(CH_2CH_2OH)_2$ | — |

-continued

| Ex. | X | Y | R¹ | M.p. [°C.] |
|---|---|---|---|---|
| 45 | 7-Cl | H,H | 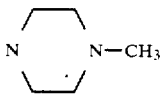 N-methylpiperazinyl | 82 |
| 46 | 7-Cl | H,H | NH—(2-pyridyl) | >270 (.HCl) |
| 47 | 7-Cl | H,H | NH—CH$_2$—CH=CH$_2$ | 198 (.HCl) |
| 48 | 7-Cl | H,H | N(CH$_3$)(Cyclohexyl) | 230 (.HCl) |
| 49 | 7-Cl | H,H | N(C$_3$H$_7$)$_2$ | 84 (.HCl) |
| 50 | 7-Cl | H,H | N(Cyclohexyl)$_2$ | >280 (.HCl) |
| 51 | 7-Cl | H,H | NH—C$_6$H$_{13}$ | 110 (.HCl) |
| 52 | 7-Cl | H,H | N—pyrrolidinyl | 260 (.HCl) |
| 53 | 7-Cl | H,H | N—piperidinyl | >260 (.HCl) |
| 54 | 7-Cl | H,H | morpholinyl | 117 |
| 55 | 7-Cl | H,H | O—C(CH$_3$)$_3$ | 90 |
| 56 | 7-Cl | O | OCH$_3$ | 102 |
| 57 | 7-Cl | O | OC$_2$H$_5$ | 109 |
| 58 | 7-Cl | O | OC$_4$H$_9$ | — |
| 59 | 7-Cl | O | OC$_5$H$_{11}$ | — |
| 60 | 7-Cl | O | OC$_6$H$_{13}$ | — |
| 61 | 6-Cl | =N—(4-Cl—C$_6$H$_4$) | H | 180 |
| 62 | 6-Cl | =N—(2,4-DiCl—C$_6$H$_3$) | H | 176 |
| 63 | 6-Cl | =N—(2,5-DiCH$_3$—C$_6$H$_3$) | H | 140 |
| 64 | 5-Cl | =N—(3CF$_3$—C$_6$H$_4$) | H | 160 |
| 65 | 6-Cl | =N—(2,4-DiCH$_3$—C$_6$H$_3$) | H | 130 |
| 66 | 5-Cl | =N—(2,4-DiCH$_3$—C$_6$H$_3$) | H | 120 |
| 67 | 6-Cl | =N-(1-piperidinyl) | H | 180 |
| 68 | 5-Cl | =N—(4-NO$_2$—C$_6$H$_4$) | H | 260 |
| 69 | 7-Cl | =N—CH$_2$—(2,6-DiCH$_3$—C$_6$H$_3$) | H | 154 |
| 70 | 6-Cl | =N—(4-CH$_3$O—C$_6$H$_4$) | H | 180 |
| 71 | 6-Cl | Cl, Cl | H | 134 |
| 72 | 6-Cl | O | OH | 238 |
| 73 | 5-Cl | O | ⊖⊕ ONa | >300 |
| 74 | 7-Cl | O | ⊖⊕ ONa | >300 |
| 75 | 7-Cl | O | ⊖⊕ ONH$_2$(CH$_3$)$_2$ | 180 |
| 76 | 5-Cl | Cl, Cl | H | 130 |
| 77 | 5-Cl | O | H | 170 |
| 78 | 7-Cl | H, H | COOH | 210 |
| 79 | 5-Cl | O | OH | 200 |
| 80 | 5-Cl | O | ⊖⊕ ONH$_2$(CH$_3$)$_2$ | >270 |
| 81 | 5-Cl | O | Cl | — |
| 82 | 6-Cl | O | Cl | 75 |
| 83 | 5-Cl | O | OCH$_3$ | — |
| 84 | 5-Cl | O | OC$_4$H$_9$ | — |
| 85 | 5-Cl | O | OC$_6$H$_{13}$ | — |
| 86 | 7-Cl | O | OCH$_2$CH(C$_2$H$_5$)C$_4$H$_9$ | — |
| 87 | 7-Cl | Cl, Cl | Cl | 135 |

-continued

| Ex. | X | Y | R¹ | M.p. [°C.] |
|---|---|---|---|---|
| 88 | 7-Cl | O | Cl | 91 |
| 89 | 6-Cl | O | ONa ⊖⊕ | >300 |
| 90 | 6-Cl | =N—(3-CF$_3$—C$_6$H$_4$) | H | 103 |
| 91 | 6-Cl | O | OCH$_3$ | — |
| 92 | 6-Cl | O | OC$_5$H$_{11}$ | — |
| 93 | 6-Cl | O | OC$_3$H$_7$ | — |
| 94 | 6-Cl | O | N(C$_2$H$_5$)$_2$ | — |
| 95 | 5-Cl | O | 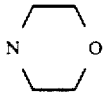 | — |
| 96 | 5-Cl | O | N N—CH$_3$ | — |
| 97 | 5-Cl | O | N(CH$_3$)$_2$ | — |
| 98 | 6-Cl | O | N—pyrrolidinyl | — |
| 99 | 6-Cl |  | N | 150 |
| 100 | 5-Cl |  | N | 174 |

The influence of various representative of the novel quinoline derivatives on the growth of unwanted and crop plants is demonstrated in the greenhouse experiments.

The vessels employed were plastic flowerpots having a volume of 300 cm³, and which were filled with a sandy loam containing about 1.5% humus. In the case of *Galium aparine*, and of rice which was cultivated for the postemergence treatment, peat was added to ensure troublefree growth. The seeds of the test plants were sown shallow, and separately, according to species.

In the preemergence treatment, the active ingredients were then immediately applied to the surface of the soil as a suspension or emulsion in water by spraying through finely distributing nozzles. The amount of active ingredient applied in this treatment varied, and was either 0.5, 1.0 or 2.0 kg/ha.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the chemicals.

For the postmergence treatment, the plants were first grown in the vessels to a height of from 3 to 15 cm, depending on growth form, before being treated. For this treatment, either plants which had been sown directly in the pots and grown there were selected, or plants which had been grown separately as seedlings and transplanted to the experiment vessels a few days before treatment. The amounts of active ingredient applied in this treatment also varied, and were either 1.0, 2.0 or 4.0 kg/ha. No cover was placed on the vessels in this treatment.

The pots were set up in the greenhouse—species from warmer areas at from 20° to 30° C., and species from moderate climates at 15° to 25° C. The experiments were run for from 3 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The prior art compounds 7-chloroquinoline (A; German Laid-Open Application DOS No. 2,322,143) and 7-chloro-4-hydroxyquinoline-2-carboxylic acid (B; U.S. Pat. No. 2,661,276) were used at a rate of 1.0 kg/ha under the same pre- and postemergence conditions for comparison purposes.

The results show that the compounds have a considerable herbicidal action on both pre- and postemergence application, and are tolerated as selective agents by various crop plants or cause at most only slight damage.

If certain crop plants tolerate, on leaf treatment, the active ingredients less well, application techniques may be used in which the agents are sprayed from suitable equipment in such a manner that the leaves of sensitive crop plants are if possible not touched, and the agents reach the soil or the unwanted plants growing beneath the crop plants (post-directed, lay-by treatment).

In view of the many application methods possible, the herbicides according to the invention may be used in a very wide range of crops for removing unwanted plants. The application rates may vary between 0.05 and 10 kg of active ingredient per hectare and more.

The following crop plants may be mentioned by way of example:

| Botanical name | Common name |
|---|---|
| *Abutilon theophrasti* | velvetleaf |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape seed |
| *Brassica napus* var. *napobrassica* |  |
| *Brassica napus* var. *rapa* | turnips |
| *Brassica rapa* var. *silvestris* |  |
| *Camellia sinensis* | tea plants |
| *Carthamus tinctorius* | safflower |
| *Carya illinoinensis* | pecan trees |
| *Cirsium arvense* | Canada thistle |
| *Citrus limon* | lemons |
| *Citrus maxima* | grapefruits |

| Botanical name | Common name |
| --- | --- |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel substituted quinoline derivatives may be mixed among themselves, or mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-methoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethyl-aniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline 3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenylcarbamate
ethyl N-3-(2'-methylphenoxycarbonylamino)-phenylcarbamate
methyl N-3-(4'-fluorophenoxycarbonylamino)-phenylthiolcarbamate
methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.2.1]-heptylthiolcarbamate
S-(2,3-dichloroallyl)-(2,2,4-trimethylazetidino)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methylα-chloro-β-(4-chlorophenyl)-propionate
methylα,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil 3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil
3-cyclohexyl-5,6-trimethyleneuracil
2-methyl-4-(3'-trifluoromethylphenyl)-tetrahydro-1,2,4-oxadiazine-3,5-dione
2-methyl-4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(1-methylpropyn-2-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-1-yl-methyl)-2-chloro-acetanilide
2-methyl-6-ethyl-N-(pyrazol-1-yl-methyl)-2-chloracetanilide
2,6-dimethyl-N-(pyrazol-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide
2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2,6-diethyl-N-(propoxyethyl)-2-chloroacetanilide
2-(2-methyl-4-chlorophenoxy-N-methoxyacetamide
2-(α-naphthoxy)-N,N-diethylpropionamide
2,2-diphenyl-N,N-dimethylacetamide
α-(3,4,5-tribromopyrazol-1-yl)-N,N-dimethylopropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyl-trifluoromethanesulfone anilide
5-acetamido-4-methyl-trifluoromethanesulfone anilide
2-propionylamino-4-methyl-5-chlorothiazole
0-(methylsulfonyl)-glycolic acid N-ethoxymethyl-2,6-dimethylanilide
0-(methylaminosulfonyl)-glycolic acid N-isopropylanilide
0-(isopropylaminosulfonyl)-glycolic acid N-but-1-yn-3-yl-anilide
0-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-0-2,4-dinitrophenylbenzaldoxime (salts)
3,5-dibromo-4-hydroxy-0-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2,4-dichlorophenyl-3'-methoxycarbonyl-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfonate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dmethylbenzyl)3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5yl)-3,3-dimethylurea 1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate
1,3-dimethyl-4-(3,4-dichlorobenzoyl)-5-(4-methylphenylsulfonyloxy)-pyrazole
2,3,5-trichloropyridinol-(4)
1-methyl-3-phenyl-5-(3'-trifluoromethylphenyl)-pyridone-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-dipyridylium dichloride
1,1'-ethylene-2,2'-dipyridylium dibromide
3-[1-(N-ethoxyamino)-propylidene]-6-ethyl-3,4-dihydro-2H-pyran-2,4-dione
3-[1-(N-allyloxyamino)-propylidene]-6-ethyl-3,4-dihydro-2H-pyran-2,4-dione
2-[1-(N-allyloxyamino)-propylidene]-5,5-dimethylcyclohexane-1,3-dione (salts)
2-[1-(N-allyloxyamino-butylidene]-5,5-dimethylcyclohexane-1,3-dione (salts)
2-[1-(N-allyloxyamino-butylidene]-5,5-dimethyl-4-methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, amides) 3,5,6-trichloro-2-pyridinyl-oxyacetic acid (salts, esters, amides)
methyl α-naphthoxyacetate
2-(2-methylphenoxy)-propionic acid (salts, esters, amides)
2-(4-chlorophenoxy)-propionic acid (salts, esters, amides)
2(-b 2,4-dichlorophenoxy)-propionic acid (salts, esters, amides)
2-(2,4,5-trichlorophenoxy)-propionic acid (salts, esters, amides)
2-(2-methyl-4-chlorophenoxy)-propionic acid (salts, esters, amides)
4-(2,4-dichlorophenoxy)-butyric acid (salts, esters, amides)
4-(2-methyl-4-chlorophenoxy)-butyric acid (salts, esters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts, esters)
gibelleric acid (salts)
disodium methylarsonate
monosodium salt of methylarsonic acid
N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
0,0-diisopropyl-5-(2-benzosulfonylaminoethyl)-phosphorodithioate 2,3-dihydro-5,6-dimethyl-1,4-dithiin-1,1,4,4-tetraoxide
5-tert.butyl-3-(2,4-dichloro-5-isopropoxyphenyl)-1,3,4-oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone anilide
1,1-dimethyl-4,6-diisopropyl-5-indanyl ethyl ketone
sodium chlorate
ammonium thiocyanate
calcium cyanamide
2-chloro-4-trifluoromethyl-3'-ethoxycarbonyl-4'-nitrophenyl ether
1-(4-benzyloxyphenyl)-3-methyl-3-methoxyurea
2-[1-(2,5-dimethylphenyl)-ethylsulfonyl]-pyridine-N-oxide
1-acetyl-3-anilino-4-methoxycarbonyl-5-methylpyrazole
3-anilino-4-methoxycarbonyl-5-methylpyrazole
3-tert.butylamino-4-methoxycarbonyl-5-methylpyrazole
N-benzyl-N-isopropyl-trimethylacetamide
methyl 2-[4-(4'-chlorophenoxymethyl)-phenoxy]-propionate
ethyl 2-[4-(5'-bromopyridyl-2-oxy)-phenoxy]-propionate
ethyl 2-[4-(5'-iodopyridyl-2-oxy)-phenoxy]-propionate
n-butyl 2-[4-(5'-iodopyridyl-2-oxy)-phenoxy]-propionate
2-chloro-4-trifluoromethylphenyl-3'-(2-fluoroethoxy)-4'-nitrophenyl ether
2-chloro-4-trifluoromethylphenyl-3-(ethoxycarbonyl)-methylthio-4-nitrophenyl ether
2,4,6-trichlorophenyl-3-(ethoxycarbonyl)-methylthio-4-nitrophenyl ether
2-[1-(N-ethoxamino)-butylidene]-5-(2-ethylthiopropyl)-3-hydroxy-cyclohex-2-en-1-one (salts)
2-[1-(N-ethoxamino)-butylidene]-5-(2-phenylthiopropyl)-3-hydroxy-cyclohex-2-en-1-one (salts)
ethyl-4-[4-(4'-trifluoromethyl)-phenoxy]-pentene-2-carboxylate
2-chloro-4-trifluoromethyl-3'-methoxycarbonyl-4'-nitrophenyl ether
2,4-dichlorophenyl-3'-carboxy-4-nitrophenyl ether (salts)
4,5-dimethoxy-2-(3-α,α,β-trifluoro-β-bromoethoxyphenyl)-3-(2H)-pyridazinone
2,4dichlorophenyl-3'-ethoxy-ethoxy-ethoxy-4'-nitrophenyl ether
2,3-dihydro-3,3-dimethyl-5-benzofuranyl-ethane sulfonate
N-[4-methoxy-6-methyl-1,3,5-triazin-2-yl-aminocarbonyl]-2-chlorobenzene sulfonamide 1-(3-chloro-4-ethoxyphenyl)-3,3-dimethylurea
ethyl 2-methyl-4-chlorophenoxy-thioacetate
2-chloro-3,5-diiodo-4-acetoxy-pyridine
1-(-4-[2-(4-methylphenyl)-ethoxy]-phenyl)-3-methyl-3-methoxyurea
2,6-dimethyl-N-(pyrazol-1-yl-methylenoxymethyl)-2-chloroacetanilide
2-methyl-6-ethyl-N-(pyrazol-1-yl-methylenoxmethyl)-2-chloroacetanilide
1(α-2,4-dichlorophenoxypropionic acid)-3-(0-methyl-carbamoyl)-anilide
1-(α-2-bromo-4-chlorophenoxypropionic acid)-3-(0-methylcarbamoyl)-anilide
2-methyl-6-ethyl-N-(pyrazol-1-yl-ethylenoxymethyl)-2-chloroacetanilide
methyl-N-dichlorofluoromethylsulfenyl-(3-(N'-dichlorofluoromethylsulfenyl-N'-phenylcarbamoyloxy)-phenyl)-carbamate
methyl-N-dichlorofluoromethylsulfenyl-(3-(N'-dichlorfluoromethylsulfenyl-N'-3-methylphenylcarbamoyloxy)-phenyl)-carbamate
N-(pyrazol-1-yl-methyl)-pyrazol-1-yl-acetic acid-2,6-dimethylanilide
N-(pyrazol-1-yl-methyl)-1,2,4-triazol-1-yl-acetic acid-2,6-dimethylanilide
2-(3-trifluoromethylphenyl)-4H-3,1-benzoxazin-4-one
2-(2-thienyl)-4H-3,1-benzoxazin-4-one It may also be useful to apply the novel compounds, either alone or in combination with other herbicides, in admixture with other crop protection agents, e.g., agents for combating pests or phytopathogenic fungi or bacteria. The compounds may also be mixed with mineral salt solutions used to remedy nutritional or trace element deficiencies. Non-phytotoxic oils and oil concentrates may also be added.

In investigations into selective herbicidal action on preemergence application in the greenhouse at a rate of 2.0 kg of active ingredient per hectare, for example the compound of Example 2 had quite a good herbicidal action and was well to acceptably tolerated by rice, sunflowers and wheat. When this compound was employed postemergence in the greenhouse for selective weed control (application rate: 2 kg/ha), it also had a considerable herbicidal action and was well or acceptably tolerated by crop plants such as oats, rice, rape and wheat.

In investigations into the herbicidal action on preemergence application in the greenhouse at 1.0 kg of active ingredient per hectare, for instance the compound of Example 4 revealed a good herbicidal action and was well and usefully tolerated by rape, rice and sorghum as examples of crop plants.

Further, the compound for instance of Example 14 exhibited, on investigations into the herbicidal action on preemergence application in the greenhouse at a rate of, for example, 1.0 kg/ha, a good herbicidal action and a consistently good selectivity in rape, rice and wheat.

The compound of Example 10 also exhibited, on preemergence application in the greenhouse at the rate of 1.0 kg/ha used by way of example, a very good herbicidal action on grassy and broadleaved unwanted plants.

The investigations into the herbicidal action on postemergence application in the greenhouse at a rate of 1.0 kg/ha, the compound of Example 10 also had a very good herbicidal action, combined with an only slight inhibition in the growth of crop plants, e.g., rice. The same active ingredient is also suitable, depending on the weed species to be combated and accordingly selected application rates, as a selective agent in other crops.

When the compound of Example 75 was applied pre- and postemergence at 0.5 and 1.0 kg/ha to important unwanted plants, it had a herbicidal action and was well tolerated by crop plants.

The compound of Example 74, applied postemergence in the greenhouse at 1.0 kg/ha, also had a good and selective herbicidal action.

Further, the compound of Example 12 combated, on postemergence application of 2.0 kg/ha, a number of grassy and broadleaved unwanted plants and was well tolerated by crop plants.

In the greenhouse experiments described above, the compound of Example 10, on pre- and postemergence application of, for example, 1.0 kg/ha, proved to have a herbicidal action far superior to that of comparative compounds A and B.

In investigations into the herbicidal action on postemergence application in the greenhouse, compound 16 at 2.0 kg/ha, and compound 1 at 4.0 kg/ha had a quite remarkable selective herbicidal action. When compounds 16 and 69 were applied preemergence in the greenhouse at a rate of 2.0 kg/ha, they exhibited a selective herbicidal action.

In greenhouse experiments with azaleas (Rhododendron simsii), it was able to be shown that for instance compound 10 regulates the shoot growth of herbaceous plants and may thus be used, depending on the application rate employed, as a growth regulator for such plants or for combating them.

In the open, compound 10 achieved, when applied preemergence at a rate of 0.5 kg/ha in experiments on small plots (the soil of which was a sandy loam having a pH of 6 and containing 1 to 1.5% humus), very good control of naturally occurring weeds, without damaging rape, winter barley or Indian corn used as examples of crop plants. The active ingredient was emulsified or suspended in water as vehicle and applied with the aid of a plot spray mounted on a tractor. Where no natural precipitate fell, the plots were sprinkler-irrigated to ensure germination and growth of crop plants and weeds. Assessment was carried out at certain intervals on the 0 to 100 scale.

We claim:

1. A dichloroquinoline derivative of the formula

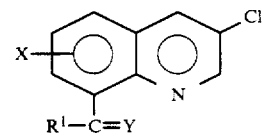

where X is chlorine in the 5-, 6- or 7 position, Y is oxygen, two hydrogen atoms, two chlorine atoms or =N—A—B, $R^1$ is hydrogen, OM or —$NR^2R^3$ where Y is oxygen; $R^1$ is OM or —$NR^2R^3$, where Y is two hydrogen atoms; $R^1$ is hydrogen if Y is two chlorine atoms and $R^1$ is hydrogen if Y is =N—A—B, where A is a direct bond or $CH_2$ and B is a phenyl or pyridine radical which is unsubstituted or substituted by chlorine, nitro, methyl, trifluoromethyl or methoxy, and $R^1$ is hydrogen, or —$NR^2R^3$, where $R^2$ and $R^3$ are identical or different and each is hydrogen, $C_1$-$C_6$-alkyl, $C_1$-$C_6$-alkenyl, $C_1$-$C_6$-hydroxyalkyl, formyl, cyclohexyl, phenyl or pyridinyl, or $R^2$ and $R^3$ together are $(CH_2)_4$, $(CH_2)_5$, $(CH_2$—O—$(CH_2)_2$ or $(CH_2$—N($CH_3$)—$(CH_2)_2$, or $R^1$ is OM, where M is a metal of main group 1 or 2 of the Periodic Table, hydrogen, $C_1-C_8$-alkyl, phenyl which is unsubstituted or substituted by halogen, nitro, $C_1-C_4$-alkyl or trihalomethyl, or $H_2N^{\oplus}R^2R^3$, where $R^2$ and $R^3$ have the above meanings, or Y and $R^1$, together with the carbon atom, are nitrile.

2. A herbicide containing a compound of the formula I as set forth in claim 1 and a solid or liquid carrier.

3. A process for combating the growth of unwanted plants, wherein the plants or the soil are treated with a compound of the formula I as set forth in claim 1.

4. A dichloroquinoline derivative of the formula I as set forth in claim 1, where X is chlorine in the 7-position.

5. A dichloroquinoline derivative of the formula I as set forth in claim 1, where X is chlorine in the 7-position, Y is oxygen, two hydrogen atoms or =N—A—B, where A is a direct bond and B is a phenyl or pyridine radical which is unsubstituted or substituted by chlorine, nitro, methyl, trifluoromethyl or methoxy, and $R^1$ is hydrogen, $-NR^2R^3$, where $R^2$ and $R^3$ are identical or different and each is hydrogen, $C_1-C_6$-alkyl, $C_1-C_6$-alkenyl, $C_1-C_6$-hydroxyalkyl, formyl, cyclohexyl, phenyl or pyridinyl, or $R^1$ is OM, where M is a metal of main group 1 or 2 of the Periodic Table, hydrogen, $C_1-C_8$-alkyl, phenyl which is unsubstituted or substituted by halogen, nitro, $C_1-C_4$-alkyl or trihalomethyl.

6. A dichloroquinoline derivative of the formula

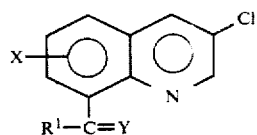

where X is chlorine in the 7-position, Y is two hydrogen atoms and $R^1$ is $-NR^2R^3$, where $R^2$ and $R^3$ are identical or different and each is $C_1-C_6$-alkyl or phenyl.

7. A dichloroquinoline derivative of the formula I as set forth in claim 1, where X is chlorine in the 7-position, Y is oxygen and $R^1$ is OM, where M is a metal of main group 1 or 2 of the Periodic Table, hydrogen or $C_1-C_8$-alkyl.

8. 3,7-Dichloro-quinoline-8-carboxylic acid.

9. 3,7-Dichloro-8cyano-quinoline.

10. A herbicide containing inert additives and, as active ingredient, a dichloro-quinoline derivative of the formula I as set forth in claim 4.

11. A herbicide containing inert additives and, as active ingredient, a dichloro-quinoline derivative of the formula I, where X is chlorine in the 7-position, Y is oxygen, two hydrogen atoms or =N—A—B, where A is a direct bond and B is a phenyl or pyridine radical which is unsubstituted or substituted by chlorine, nitro, methyl, trifluoromethyl or methoxy, and $R^1$ is hydrogen, $-NR^2R^3$, where $R^2$ and $R^3$ are identical or different and each is hydrogen, $C_1-C_6$-alkyl, $C_1-C_6$-alkenyl, $C_1-C_6$-hydroxyalkyl, formyl, cyclohexyl, phenyl or pyridinyl, or $R^1$ is OM, where M is a metal of main group 1 or 2 of the Periodic Table, hydrogen, $C_1-C_8$-alkyl, phenyl which is unsubstituted or substituted by halogen, nitro, $C_1-C_4$-alkyl or trihalomethyl.

* * * * *